(12) United States Patent
Magnusson et al.

(10) Patent No.: US 8,974,227 B2
(45) Date of Patent: *Mar. 10, 2015

(54) DENTAL COMPONENT, A DENTAL FIXTURE AND A DENTAL IMPLANT

(75) Inventors: Daniel Magnusson, Hönö (SE); Josef Saltell, Göteborg (SE)

(73) Assignee: Dentsply International Inc., York, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/613,065

(22) Filed: Sep. 13, 2012

(65) Prior Publication Data

US 2013/0244203 A1 Sep. 19, 2013

Related U.S. Application Data

(60) Provisional application No. 61/534,524, filed on Sep. 14, 2011.

(30) Foreign Application Priority Data

Sep. 14, 2011 (EP) .................................. 11181247

(51) Int. Cl.
*A61C 8/00* (2006.01)

(52) U.S. Cl.
CPC ............ *A61C 8/0066* (2013.01); *A61C 8/0054* (2013.01); *A61C 8/0068* (2013.01); *A61C 8/0069* (2013.01); *A61C 8/0089* (2013.01); *A61C 8/0001* (2013.01); *A61C 8/008* (2013.01); *A61C 2008/0046* (2013.01)
USPC ....................................... 433/173; 433/201.1

(58) Field of Classification Search
USPC ....................................... 433/172–176, 201.1
See application file for complete search history.

(56) References Cited

U.S. PATENT DOCUMENTS

| 5,904,483 | A | * | 5/1999 | Wade ............................ 433/173 |
| 6,116,904 | A | | 9/2000 | Kirsch et al. |
| 6,227,859 | B1 | | 5/2001 | Sutter |
| 6,332,777 | B1 | | 12/2001 | Sutter |
| 6,382,977 | B1 | | 5/2002 | Kumar |
| 6,461,160 | B1 | | 10/2002 | Sutter |
| 6,726,480 | B1 | * | 4/2004 | Sutter ........................... 433/173 |

(Continued)

FOREIGN PATENT DOCUMENTS

| EP | 1444964 A2 | 5/1998 |
| WO | 0105326 A1 | 1/2001 |

(Continued)

OTHER PUBLICATIONS

International Search Report, Application No. 2012/067643, Search completed Dec. 20, 2012.

(Continued)

*Primary Examiner* — Edward Moran
(74) *Attorney, Agent, or Firm* — David A. Zdurne; Douglas J. Hara; Leana Levin

(57) ABSTRACT

The present invention employs a dental component that includes at least one first indexing element and at least one second indexing element having an apical end located apically of the apical end of said first indexing element, wherein the second indexing element is designed to present a play with mating features of a dental fixture.

6 Claims, 9 Drawing Sheets

(56) References Cited

U.S. PATENT DOCUMENTS

| | | | |
|---|---|---|---|
| 7,104,797 B2* | 9/2006 | Rassoli | 433/173 |
| 7,108,510 B2 | 9/2006 | Niznick | |
| 2003/0148246 A1* | 8/2003 | Lustig et al. | 433/172 |
| 2005/0065525 A1 | 3/2005 | Aringskog et al. | |
| 2005/0136380 A1 | 6/2005 | Niznick | |
| 2005/0287496 A1* | 12/2005 | Niznick | 433/173 |
| 2007/0059666 A1* | 3/2007 | Zickman et al. | 433/173 |
| 2007/0281278 A1* | 12/2007 | Jorneus et al. | 433/173 |
| 2008/0096168 A1* | 4/2008 | Schonenberger | 433/174 |
| 2009/0035721 A1* | 2/2009 | Garcia Saban et al. | 433/174 |
| 2009/0123890 A1 | 5/2009 | Purga et al. | |
| 2010/0184002 A1* | 7/2010 | Ranck et al. | 433/172 |
| 2012/0178049 A1 | 7/2012 | Holmstrom et al. | |

FOREIGN PATENT DOCUMENTS

| | | |
|---|---|---|
| WO | 0128451 A1 | 4/2001 |
| WO | 2005058178 A2 | 6/2005 |
| WO | 2009149881 A1 | 12/2009 |
| WO | 2011023750 A2 | 3/2011 |

OTHER PUBLICATIONS

International Search Written Opinion, Application No. 2012067643, Mail date Jan. 7, 2013.

European Search Report, Application No. 11181247.5, Search completed Jun. 22, 2012.

* cited by examiner

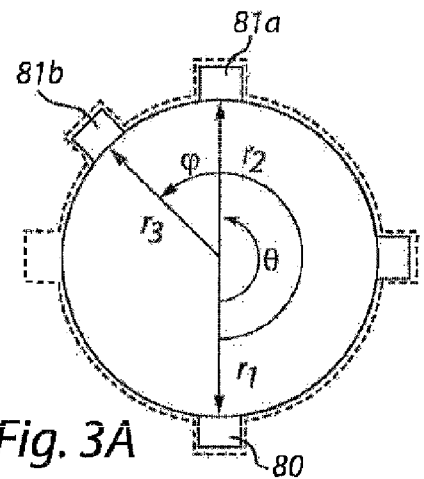
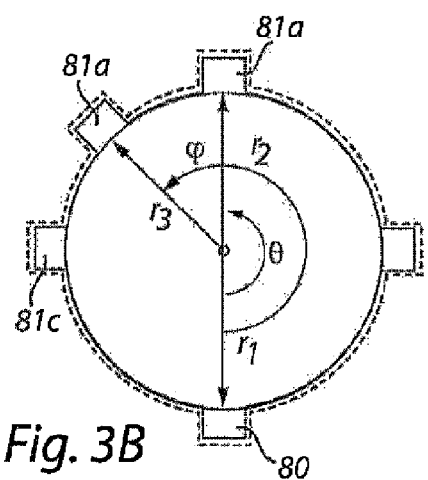
Fig. 3A    Fig. 3B
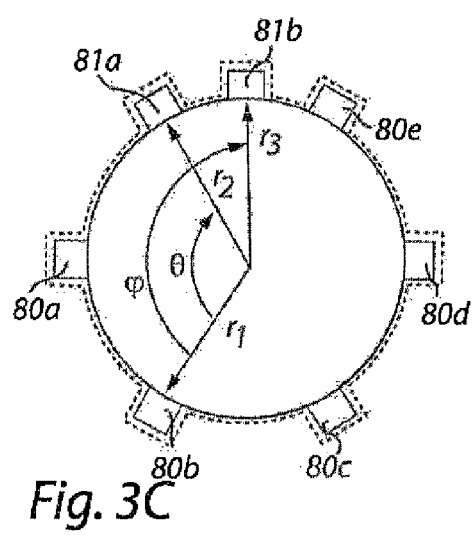
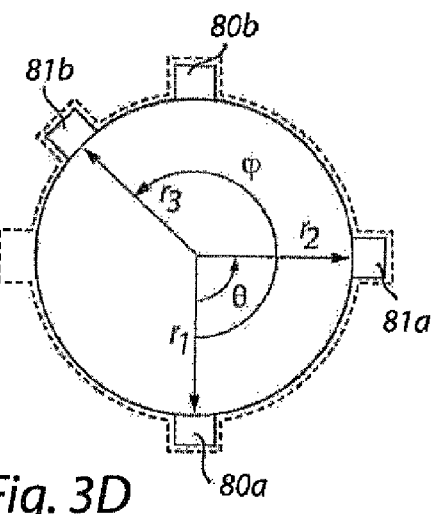
Fig. 3C    Fig. 3D
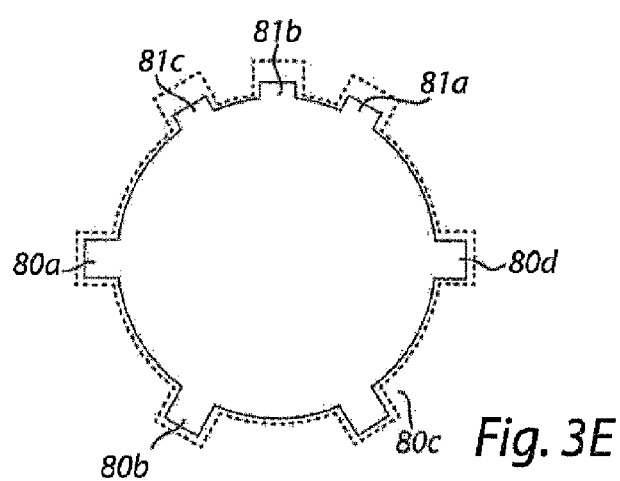
Fig. 3E

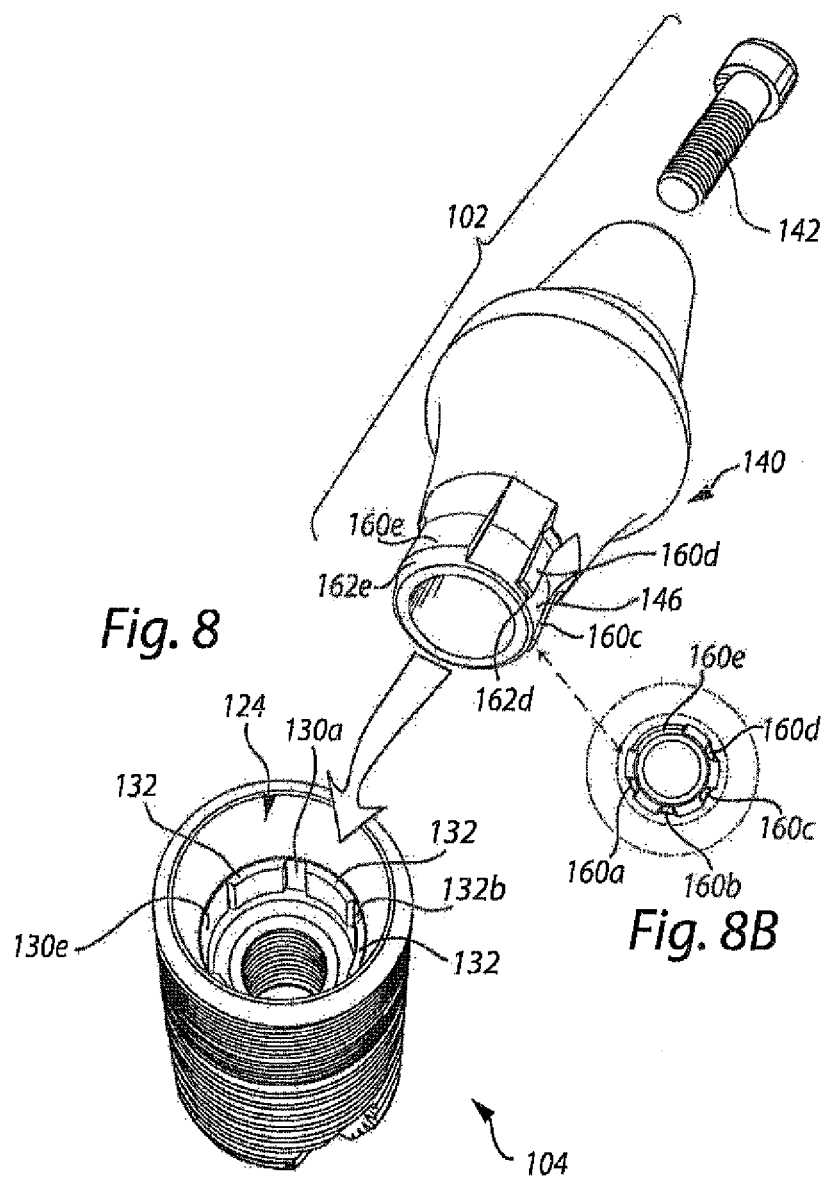
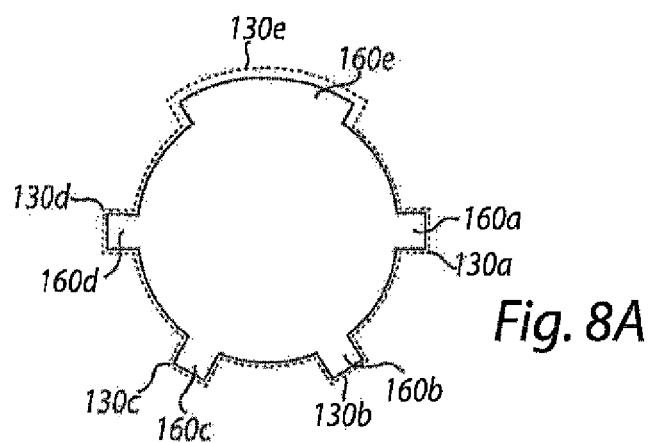

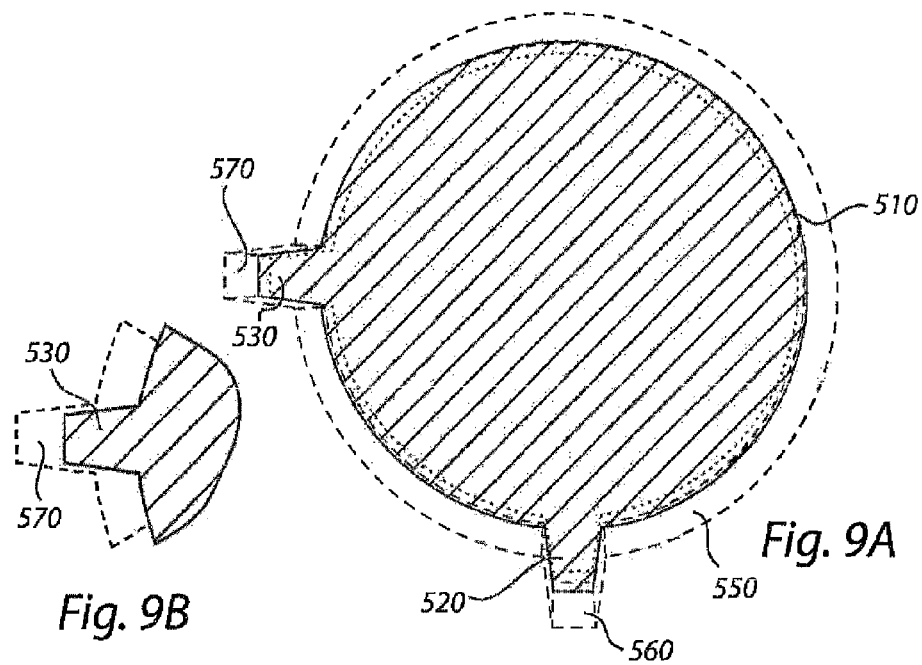
*Fig. 9B*  *Fig. 9A*
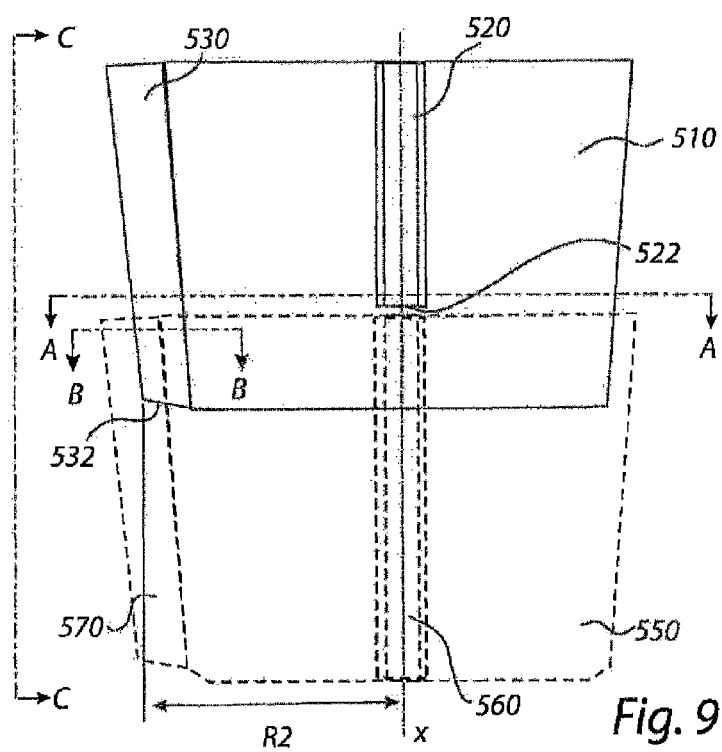
*Fig. 9*

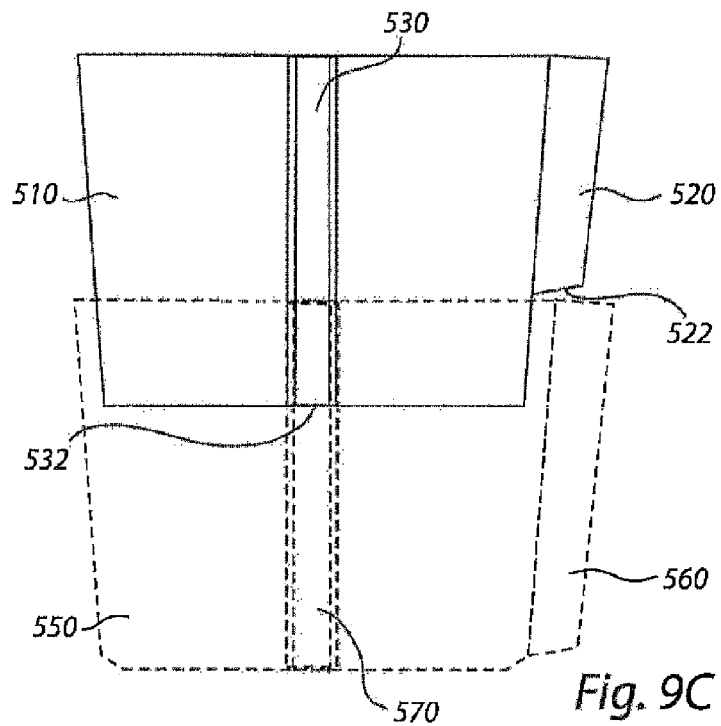
Fig. 9C
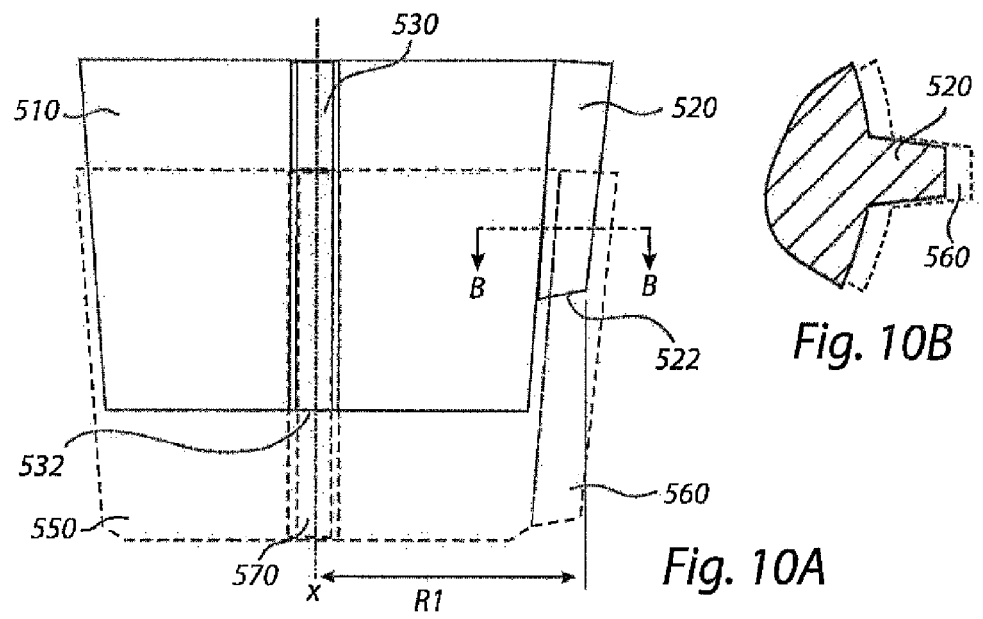
Fig. 10B
Fig. 10A

DENTAL COMPONENT, A DENTAL FIXTURE AND A DENTAL IMPLANT

RELATED APPLICATIONS

This patent application claims the benefit of and priority to EP Application Ser No. 11181247.5, filed on Sep. 14, 2011 and U.S. Provisional Patent Application Ser. No. 61/534,524, filed on Sep. 14, 2011, which are herein incorporated by reference for all purposes.

TECHNICAL FIELD

The present invention relates to a dental component comprising a fixture engagement portion for engaging the dental component with a dental fixture adapted to be inserted into a jawbone or for engaging the dental component with a fixture replica. The invention also relates to a dental fixture adapted to be inserted into a jawbone, and to a dental implant comprising a dental fixture and a dental component connectible to the dental fixture

BACKGROUND OF THE INVENTION

Dental implant systems are widely used for replacing damaged or lost natural teeth. In such systems, a dental fixture is placed in the jawbone of a patient in order to replace the natural tooth root. An abutment structure comprising one or several parts may then be attached to the fixture in order to build up a core for the part of the prosthetic tooth protruding from the bone tissue, through the soft gingival tissue and into the mouth of the patient. On said abutment, the prosthesis or crown may finally be seated.

The final prosthesis should be sized and configured so as to naturally fit with the remaining teeth of the patient, both for functionality and aesthetics. To this end a dental technician may try out a proper prosthesis for the individual patient, using a model of the jaw of the patient, said model including the fixture. The dental technician may also digitally work out a proper prosthesis based on a digital model of the jaw of the patient either with a fixture already installed or prior to such installation. The dental technician may also modify a prefabricated abutment to match the contour of the soft gingival tissue.

Some abutment/fixture interfaces are designed with radial indexing protrusions and matching indexing recesses. For instance, the abutment may be provided with the radial protrusions which are adapted to mate with corresponding recesses in the fixture when the two components are to be joined. Dentists sometimes experience difficulties in aligning the abutment so that the protrusions mate with the recesses in the fixture. Indeed the dentist may have to rotate the abutment back and forth until the correct orientation is found and the protrusions engage with the recesses.

An object of the invention is to make it easier for dentists to connect a dental component, such as an abutment, to a fixture compared to the currently available solutions.

This and other objectives, which will become apparent in the following, are achieved by the dental component, the dental fixture and the dental implant as defined in the accompanied claims.

SUMMARY OF THE INVENTION

The present invention is based on the insight that when connecting a dental component to a dental fixture, one or more leading indexing elements may be used for guiding the dental component into the correct rotational position relative to the fixture before one or more subsequent trailing indexing elements are engaged to form the final rotational lock. The invention is also based on the insight that a comparatively large play for engaging the leading indexing element further facilitates the connecting procedure.

According to a first aspect of the invention, a dental component is provided. The dental component comprises a fixture engagement portion for engaging the dental component with a dental fixture adapted to be inserted into a jawbone or for engaging the dental component with a fixture replica, the fixture engagement portion having a geometrical central axis and being provided with at least one radially projecting first indexing element having an apical end, and at least one radially projecting second indexing element having an apical end located apically of the apical end of said first indexing element, wherein the radially most distant area of the apical end of the second indexing element is located at a shorter radial distance from said central axis than the radially most distant area of the apical end of the first indexing element, and/or wherein, the apical end of the second indexing element has, compared to the apical end of the first indexing element, a smaller dimension in the circumferential direction of the fixture engagement portion.

This has the effect that when the dental component is to be connected with the fixture and thus moved towards the fixture, the at least one second indexing element will be the first to mate with the fixture. In this way, the location finding function of the indexing elements will be concentrated to a smaller part of the circumference of the fixture engagement portion. The dentist will experience a more distinct perception when said at least one second indexing element falls into place with a corresponding receiving portion of the fixture, compared to if all indexing elements around the circumference of the fixture engagement portion were to connect simultaneously as in the prior art.

According to at least one example embodiment, said at least one second indexing element is a single second indexing element or at least two second indexing elements asymmetrically distributed along the circumference of the fixture engagement portion. Since the second indexing elements is either a single one or at least two which are asymmetrically distributed along the circumference of the fixture engagement portion, a component/fixture interface may, if desired, be provided in which the second indexing element(s) only have one correct rotational position, thereby avoiding that the dentist connects the dental component to the fixture in an incorrect rotational orientation. Furthermore, having a single one or several asymmetrically distributed second indexing elements may provide a distinct indication to the dentist when corresponding indexing element(s) in the fixture is/are engaged. It is believed that, at the moment of engagement, the engagement perceived by the dentist will be more clear than if a dental component would have evenly distributed second indexing elements.

According to at least one example embodiment, said at least one first indexing element is circumferentially separated from any one of said one or more second indexing elements. This means that said first indexing element is located at a different position along the circumference of the fixture engagement portion than any one of the second indexing elements. In other words, a radius drawn from the geometrical central axis to the first indexing element extends in a different direction from said axis than any radii drawn from said axis to the second indexing elements.

Normally, a dental fixture has equally dimensioned recesses for receiving radially projecting indexing elements of a dental component. As mentioned above, the apical end of said at least one second indexing element of the dental component may have a smaller dimension in the circumferential (transverse) direction compared to the apical end of said at least one first indexing element. Additionally or alternatively, the radially most distant area of the apical end of said at least one second indexing element may be located at a shorter distance from the central axis of the fixture engagement portion than the radially most distant area of the apical end of the first indexing element. This is advantageous because the second indexing element will be received in its receiving recess with a relatively large play. For instance, if apical end of the second indexing element has a smaller dimension in the circumferential (transverse) direction compared to the apical end of the first indexing element, than the apical end of the second indexing element will be received with a larger play in the transverse direction. The at least one second indexing element, having its apical end located apically of the apical end of the at least one first indexing element, will be received by the corresponding recess before the trailing first indexing element is received by its corresponding recess in the fixture. The relatively large play facilitates for the dentist to get the second indexing element into engagement with the corresponding recess in the fixture. Thus, at this stage, when only the apical end of the second indexing element has been engaged, a small rotational movement of the dental component relative to the fixture may be possible. However, when the at least one first indexing element follows to engage with its corresponding recess, since it is suitably more accurately dimensioned to fit closely in its recess, the dental component will become rotationally locked when the at least one first indexing element has entered in engagement with is mating recess.

In an example presented above the apical end of the second indexing element had a smaller dimension in the circumferential direction than the apical end of the first indexing element. Thus, the apical end of the second indexing element can be regarded as narrower than the apical end of the first indexing element. Additionally or alternatively, the apical end of the second indexing element may have a smaller dimension in the radial direction of the fixture engagement portion compared to the apical end of the first indexing element. In such an example, the apical end of the second indexing element can be regarded as flatter than the apical end of the first indexing element, thereby enabling a larger radial play when received in the fixture.

However, although a play, such as a radial and/or transverse play, can be achieved by underdimensioning the apical end of the second indexing element in at least one direction, there are other alternatives as well. Indeed, when viewed as isolated items, the first indexing element and the second indexing element could be identically dimensioned in all directions. The desired effect can still be achieved by placing them at selected locations of a fixture engagement portion. One example is on an apically tapering fixture engagement portion. By placing the apical end of the second indexing element apically of the apical end of the first indexing element, the apical end of the second indexing element will be located at a shorter distance from the central axis because of the tapering fixture engagement portion, even if the first and second indexing elements are essentially identical (apart from there placements on the fixture engagement portion). This will have the result that the apical end of the second indexing element will approach and be received by a recess in the fixture with a radial play while the apical end of the first indexing element will be received by a smaller radial play, if any. Another example is a non-circular, such as a slightly oval fixture engagement portion, having a large diameter and a short diameter. By placing the second indexing element at the short diameter, its radial distance to the central axis will be shorter than the radial distance of the first indexing element (placed at the long diameter). The slightly oval fixture engagement portion could be arranged in a circular component engagement portion of the fixture having receiving indexing recesses, with the result that the second indexing element will have a larger radial play than first indexing element.

It should be understood that for achieving the location finding function of the second indexing element it is enough if the apical end of the second indexing element will have the desired play when received in the fixture. For instance the second indexing element may be wedge-shaped, having a smaller sized apical end than the apical end of the first indexing element, but having a coronal end with similar dimension as the coronal end of the first indexing element. However, the entire second indexing element may suitably be arranged to provide a play. Thus, the entire second indexing element, not only the apical end thereof, may suitably be narrower and/or flatter than the first indexing element.

According to at least one example embodiment, said radially projecting second indexing element comprises at least two radially projecting second indexing elements, each one having an apical end of smaller dimension in the circumferential direction compared to the apical end of the first indexing element, and/or the radially most distant area of the apical end of each one of the second indexing elements being located at a shorter radial distance from said central axis than the radially most distant area of the apical end of the first indexing element. Having two radially projecting second indexing elements rather than just one may increase the stability of the dental component, with little (if any) compromise of the distinct perception experienced by the dentist when the second indexing elements fall into place.

Suitably, the apical ends of said at least two second indexing elements are arranged at substantially the same level in the apical-coronal direction.

Also, in connection with dental components having some asymmetrical features which should have an intended rotational orientation relative to the fixture and the surrounding contours in the oral cavity, it may be advantageous to have at least two second indexing elements, as will be explained.

In some dental implant assemblies, there may be a dental component/fixture-interface in which the dental component should only be positioned in one way relative to the fixture, e.g. an abutment having a sloped portion matching the sloped head portion of a fixture. This is one type of asymmetrical superstructure, in which an asymmetrical feature should be positioned in a desired rotational relationship to either or both of the fixture and the jawbone with surrounding teeth. Also for patient-specific or customized superstructures, such as a customized abutment, such superstructure may often be made with a certain intended rotational orientation relative to the fixture and surrounding contours. At least one example embodiment of a dental component which takes into account the above is presented in the following.

Thus, according to at least one example embodiment, the fixture engagement portion of the dental component has a geometrical central axis, wherein a radius from said central axis to the centre of one of said at least two second indexing elements and a radius from said central axis to the centre of said first indexing element form a first angle, wherein a radius from said central axis to another one of said at least two second indexing elements and said radius from said central axis to the centre of said first indexing element form a second angle, wherein said second angle is different from said first angle and from any angle being a multiple of said first angle. A multiple is the product of a quantity by an integer. In other words, $\phi \neq n\theta$, where $\theta$ is the first angle, $\phi$ is the second angle and n is a positive integer.

Since said second angle is different from said first angle (and any multiple thereof) an asymmetry is achieved. Only by rotating the dental component a full 360° can the first and second indexing elements obtain the same positional distribution relative to the surrounding environment. This is in contrast to a symmetrical distribution of indexing elements; for instance, a component having four symmetrically distributed indexing elements can be rotated 90° to obtain the same positional distribution as before relative to the surrounding environment. The asymmetry provided in the present example embodiment reduces the risk of the second indexing elements getting caught in incorrect indexing elements in the fixture.

According to at least one example embodiment, the axial extension of the indexing elements is such that the first and second indexing elements are intersected by a common geometrical plane which is perpendicular to the central axis of the fixture engagement portion. Thus, apart from having the apical ends located at different apical positions, the first and second indexing elements may have substantially the same configuration which may be advantageous from a manufacturing perspective. Furthermore, although the dental component may only have one specific rotational orientation in one type of fixture, it could be allowed to have other rotational orientations in other types of fixtures, in which case the mating indexing elements in the fixture could receive any one of the first and second indexing elements of the dental component. Such freedom of choice would be more complicated if the first and second indexing elements are completely separated in the axial direction of the fixture engagement portion.

According to at least one example embodiment, said at least one radially projecting first indexing element comprises at least two radially projecting first indexing elements, wherein in the circumferential direction of the fixture engagement portion, said at least one second indexing element is interposed between two of said first indexing elements. Thus, there is at least one geometrical plane which is perpendicular to the central axis of the fixture engagement portion and which extends through the first indexing elements as well as through the at least one second indexing element. The coronal extension of the at least one second indexing element may suitably be to the same axial level as the coronal extension of the first indexing elements. Alternatively, the coronal extension of the at least one second indexing element may be longer or shorter than the coronal extension of the first indexing elements.

The asymmetrical distribution of the indexing elements comprising at least two first and at least two second indexing elements is reflected in at least one example embodiment, according to which the spacing between said two second indexing elements is different from the spacing between any two of said first indexing elements. The two second indexing elements do not have to lie next to each other. There may be one or more first indexing elements which are placed between said two second indexing element. Also, if there are more than two second indexing elements, some of them may be spaced at the same distance as the spacing between first indexing elements, as long as there can be identified one pair of second indexing elements having a different spacing. The advantage of this asymmetry will now be explained. Assuming the dental component is to be connected to a dental fixture having corresponding mating third and fourth indexing elements, wherein the third indexing elements are designated to mate with the first indexing elements of the dental component while the fourth indexing elements are designated to mate with the second indexing elements of the dental component, then there will be only one correct rotational orientation. Since the apical ends of the second indexing elements will be leading and be the first to form contact with the dental fixture, because of the distinct spacing between said pair of second indexing elements these cannot inadvertently be mated with the differently spaced third indexing elements.

In order for the at least one second indexing element to perform a guiding or leading function and the at least one trailing first indexing element to follow with a final rotational locking function, it is not necessary for the second indexing element to be at the same coronal-apical level as the first indexing element. The entire second indexing element may be located apically of the apical end of the first indexing element. For instance, the second indexing element may be a short protrusion or recess at an apical sub-portion of the fixture engagement portion, while the apical end of the first indexing element is located coronally thereof, at a coronal sub-portion of the fixture engagement portion. Once the second indexing element has engaged with a matching indexing element in the fixture, the dental component will continue its relative movement towards the fixture and eventually the first indexing element will also engage a matching indexing element (it is assumed that the indexing element in the fixture receiving the leading second indexing element is long enough to allow said continued motion of the dental component). Thus, in view of the above discussion, according to at least one example embodiment, there is at least one geometrical plane which is perpendicular to the central axis of the fixture engagement portion and which is located apically of the at least one first indexing element and coronally of the at least one second indexing element.

According to at least one example embodiment, said at least one second indexing element is arranged as at least three radially projecting second indexing elements, interposed between two of said first indexing elements, wherein each one of said at least three second indexing elements has an apical end which is located apically of the apical ends of said first indexing elements. This provides increased stability when the dentist intends to find of the correct rotational orientation of the dental component in the fixture.

Thus, it should be understood that said at least one second indexing element may, for instance, be two, three, four or more indexing elements.

According to at least one example embodiment, the fixture engagement portion of the dental component comprises a cylindrical surface from which said at least one first indexing element and said at least one second indexing element project radially. This is advantageous from a manufacturing point of view. However, it is conceivable to have the indexing elements project radially from other surfaces as well, e.g. from a tapered surface. As previously explained, if the indexing elements are placed on a tapered surface, there dimensions could be identical as long as the apical end of the second indexing element is placed apically of the apical end of the first indexing element (since this will bring the apical end of the second indexing element closer to the central axis of the fixture engagement portion resulting in a larger play when mating with a fixture).

According to at least one example embodiment, the number of first indexing elements is greater than the number of second indexing elements. While the number of second indexing elements may suitably be two or three, the trailing first indexing elements which complete the rotational locking may suitably be more for increased strength. This may be particularly advantageous if the dental component is a driver, wherein the indexing elements are adapted to transfer a torque to the dental fixture when driving it into the jawbone.

According to at least one example embodiment, the apical end of at least one of said at least one second indexing element is provided with a chamfer. The chamfer may facilitate mating with an indexing element (such as a groove) in the dental fixture. Another benefit is found when the dental component is provided with two asymmetrically distributed second indexing elements, as will be explained in the following.

When the fixture engagement portion of the dental component is inserted into the fixture, the dentist will rotate the dental component in order to align the indexing elements of the dental component with mating indexing elements of the fixture. The provision of the two second indexing elements, at least partly reduces the risk of one of those indexing elements engaging with the wrong indexing element in the fixture. Nevertheless, if a second indexing element, despite the supporting function of the other second indexing element, accidently drops into the wrong indexing element (such as a groove) in the dental fixture upon rotation of the dental component, when the dentist continues applying a rotating force onto the dental component the provision of a chamfer on that second indexing element will facilitate lifting that second indexing element out of the temporary incorrect engagement.

According to at least one example embodiment said at least one first indexing element and said at least one second indexing element have an elongate extension in the coronal-apical direction. This provides additional strength to the rotational lock compared to if the radially projecting indexing elements would have a shorter extension.

According to at least one example embodiment, the dental component is a component selected from the group consisting of an abutment, an abutment replica, an abutment blank, a customized abutment, a scan abutment, a digital transfer coping, an impression pick-up element, a healing cap and a driver.

For instance, a customized abutment may have a shape which is adapted to the contours of the surrounding tissue and teeth of the patient, in which case it is advantageous if the dentist can easily fit the customized abutment in the intended rotational orientation.

A digital transfer coping having some distinguishing feature indicating its rotational orientation and being connected to a dental fixture may be scanned, and a digital file is then sent to an abutment manufacturer. The digital file will contain information about the position and orientation of the distinguishing feature and thus also the position and orientation of the dental fixture.

A driver having a distinctive marking may be used as an indication to determine if the fixture has been inserted at a desired orientation relative to the jawbone and other surrounding features in the oral cavity. For instance, the fixture may have a sloping coronal end. The driver may be intended to be inserted such that the distinctive marking is aligned with the very top of the sloping end of the fixture. Thus, during rotation of the fixture into the jawbone, the dentist will know the rotational orientation of the fixture and its sloping end by looking at the distinctive marking. It is therefore advantageous if the dentist can easily fit the driver into the intended position relative to the fixture.

According to a second aspect of the invention, a dental implant is provided. The dental implant comprises a dental component comprising a fixture engagement portion provided with at least one first indexing element having an apical end, and at least one second indexing element having an apical end, a dental fixture adapted to be inserted into a jawbone and comprising a component engagement portion adapted to mate with said fixture engagement portion, the component engagement portion being provided with at least one third indexing element having a coronal end, and at least one fourth indexing element having a coronal end, wherein the apical end of the second indexing element is located apically of the apical end of the first indexing element and/or the coronal end of the fourth indexing element is located coronally of the coronal end of the third indexing element, wherein the first indexing element is only enabled to mate with the third indexing element after the second indexing element has mated with the fourth indexing element, wherein any play between the first indexing element and the mating third indexing element is smaller than a play between the second indexing element and the fourth indexing element, whereby a tighter fit is provided between the first and third indexing elements compared to the fit between the second and fourth indexing elements.

Thus, the second and fourth indexing elements will act to guide the dental component into a desired rotational orientation relative to the fixture. Once this rotational orientation has been found, and the dental component is continued to be displaced apically, the first and third indexing element will then engage each other to provide a final rotational stop. While the first and third indexing elements, suitably, form a relatively tight fit in order to reduce the risk of small rotational movements between the dental component and the dental fixture, the fit between the second and fourth indexing elements is provided with a relatively large play (e.g. a lateral play or a radial play).

The play between the second and fourth indexing elements makes it easy for the dentist to find the desired rotational orientation as the second indexing element will more easily be received by the fourth indexing element than what would be the case without such a play. The tight fit between the first and third indexing elements makes sure that the same rotational position is obtained throughout a multi-step procedure, e.g. making an impression with a dental component (such as a transfer coping) connected to the fixture, making a model based on the impression, making another dental component (such as an abutment) based on the model and connecting the latter dental component to the dental fixture. A potential rotational error, although small, in each step, may in the end result in a large rotational error. The tight fit between the first and third indexing elements reduces the risk of rotational errors in each step.

It should be understood that the larger play between the second and fourth indexing elements may be obtained in a variety of ways. The second indexing element does not necessarily have to be of smaller dimension than the first indexing element. Indeed the second and fourth indexing elements may be of larger dimensions than the first and third indexing elements, as long as the relationship between the second and fourth indexing elements is such that a larger play is obtained than any play between the first and third indexing elements.

According to at least one example embodiment, said first and second indexing elements are provided as radial projections which project from a surface of the fixture engagement portion of the dental component, and wherein said third and fourth indexing elements are provided as radial depressions in a surface of the component engagement portion of the dental fixture. However, it would be conceivable to have it the other way around, i.e. the projections on the fixture and the depressions in the dental component. Other mixed alternatives are also conceivable as long as the second and fourth indexing elements mate before the mating of the first and third indexing elements.

According to at least one example embodiment, the first, second, third and fourth indexing elements are distributed along the circumference of the fixture engagement portion and the component engagement portion, respectively, in such way that the dental component can only mate in one rotational orientation with respect to the dental fixture. As previously, explained, in some cases it is self-evident which is the correct rotational orientation, wherein it may suffice to facilitate the engagement of the dental component to the dental fixture by having some indexing elements mating before others. In other cases, when the correct rotational orientation is not self-evident, it may be advantageous to prevent the dentist or other person to inadvertently arrange the dental component in an incorrect rotational orientation relative to the dental fixture.

According to at least one example embodiment, said at least one second indexing element is a single second indexing element or at least two second indexing elements asymmetrically distributed along the circumference of the fixture engagement portion.

According to at least one example embodiment, said at least one first indexing element is circumferentially separated from the one or more second indexing elements, and said at least one third indexing element is circumferentially separated from the one or more fourth indexing elements.

According to at least one example embodiment, the dental component of the dental implant according to the second aspect of the invention, is a dental component having the features discussed in connection with the first aspect of the invention. The fixture of the dental implant may have features matching/associated with the features of the dental component.

According to a third aspect of the invention, a dental fixture adapted to be inserted into a jawbone is provided. The dental fixture comprises a component engagement portion adapted to mate with a fixture engagement portion of a dental component, the component engagement portion having a geometrical central axis and being provided with at least one radially indenting apical indexing element having a coronal end, and at least one radially indenting coronal indexing element having a coronal end which is located coronally of the coronal end of the apical indexing element, wherein the radially most distant area of the coronal end of the coronal indexing element is located at a larger distance from said central axis than the radially most distant area of the coronal end of the apical indexing element, and/or wherein the coronal end of the coronal indexing element has, compared to the coronal end of the apical indexing element, a larger dimension in the circumferential direction of the component engagement portion.

Thus, the dental fixture of the third aspect of the invention is based on the corresponding principle as the dental component of the first aspect of the invention and the dental implant of the second aspect of the invention. Assuming the dental fixture is to be mated with a dental component having indexing elements in the form of substantially equally sized radial projections to be received by the indexing elements of the dental fixture, the following may be noted. Since the at least one coronal indexing element has a coronal end located coronally of the at least one apical indexing element, the coronal indexing element will be the first to receive a mating projection of the dental component, thus acting as a guide before the apical indexing element receives its mating projection to complete the insertion. Because the coronal end of the coronal indexing element has a larger dimension or located at a larger radial distance from the central axis, it will provide for a larger play for the radial projection entering the coronal indexing element, thereby facilitating the insertion. The smaller play (if any) at the apical indexing element will provide a tighter rotational lock.

According to at least one example embodiment, said at least one apical indexing element is circumferentially separated from any one of said one or more coronal indexing elements.

According to at least one example embodiment, said at least one coronal indexing element is a single coronal indexing element or at least two coronal indexing elements asymmetrically distributed along the circumference of the component engagement portion.

The dental fixture according to the third aspect of the invention, may have any one of the features of dental fixtures mentioned in connection with the first and second aspects of the invention and/or any one of the features of dental fixtures mentioned in the following.

As mentioned above, a dental implant comprises a dental fixture and a dental component.

A dental fixture is for use as the anchoring member of a dental prosthesis. To this end, the dental fixture is insertable into a pre-prepared bore hole in the bone tissue of a jawbone (maxilla or mandible) at a site where the dental prosthesis is required. The dental fixture is normally rotated into the bore hole.

For screw-type dental fixtures the bore hole may be provided with internal threads in advance or may be left un-tapped with the dental fixture provided with a self-tapping capacity, e.g. by the provision of one or more axially-extending cutting recesses, edges or notches, etc in the fixture thread. For instance, an apical end portion of the fixture may be provided with 2-4 cutting recesses, such as 3 cutting recesses. Other number of cutting recesses are readily conceivable.

A dental component may, as discussed previously be any one of a number of different components. One example is a driver for inserting the dental fixture into the jawbone. Another example is a superstructure for connecting a prosthetic part to the fixture. The superstructure may comprise an abutment, spacer or other transmucosal component which engages to the dental fixture to bridge the gingiva overlying the maxilla or mandible. The prosthetic part, e.g. a crown, bridge or denture may be secured to the abutment. There are various other forms that the superstructure can take. For instance, the prosthetic part may be secured directly to the dental fixture.

The term "coronal" is here and throughout this application used to indicate a direction towards a head end or trailing end of the dental implant. For instance, in a situation where a dental abutment is connected to a dental fixture, the coronal direction of the abutment would be a direction towards the part of the abutment being directed away from the fixture. Conversely, the term "apical" indicates a direction towards an insertion or leading end of the component. Thus, apical and coronal are opposite directions. Furthermore, the terms "axial", "axial direction" or "axially" are used throughout this application to indicate a direction taken from the coronal end to the apical end, or vice versa. The terms "radial", "radial direction" or "radially" indicate a direction perpendicular to the axial direction.

A blind bore or socket may extend apically into the fixture body from the coronal end to an end surface in-between the apical and coronal ends of the fixture body for a superstructure to be secured to the fixture. The socket may comprise an internally-threaded section for screw connection of the dental component to the fixture. A rotational lock for the dental component may be provided in the socket, such as an internal polygonal side wall, e.g. hexagonal, or alternatively one or more protrusions from or indentation in the wall of the socket. A section of the socket, such as the coronal section, may be tapered towards the apical end. The tapered section is suitably arranged coronally of the internally-threaded section.

The fixture may be used in a one stage procedure or a two stage procedure. In a one stage procedure a healing or temporary abutment is connected to the fixture to form the gingival tissue, and after a healing period the healing or temporary abutment is replaced by a permanent abutment. For a two stage procedure the fixture is provided with a cover screw and the gingival tissue is sutured over the fixture and cover screw, and after a healing period the tissue is opened up and an abutment is connected to the fixture after removal of the cover screw.

The dental fixture may have a conically tapering end portion which tapers towards the coronal end. The axial extent of this coronal end portion is small compared to the total length of the fixture, as an example no more than 4% of the total length, such as in the range of 1.5%-3.7%. The coronal end portion may suitably be provided without a threaded surface, e.g. having a smooth or a roughened (such as blasted) surface.

The fixture may have a substantially flat coronal end surface which is perpendicular to the longitudinal axis of the fixture. Alternatively, the coronal end surface may have a sloped contour relative to the longitudinal axis of the fixture, e.g. such that when positioned within the jawbone the length of the fixture is larger on a lingual side and shorter on a buccal side of the fixture. Another alternative is a saddle-shaped or wave-like coronal end surface.

The length of the dental fixture may be in the range of 5-19 mm, depending on the clinical situation. The outer diameter of the dental fixture may suitably be in the range of 2-6 mm, such as 3-5 mm.

The fixture may be substantially cylindrical or slightly tapering from the coronal end towards the apical end. If the fixture has a slight tapering, the core of the fixture and the outer periphery defined by e.g. thread tops may have the same or different angle of taper. Furthermore, the core of the fixture may be cylindrical while the thread tops describe a conicity or, conversely, the core of the fixture may be tapered while the thread tops describe a generally cylindrical geometry. Alternatively, the fixture may comprise a combination of one or more cylindrical and/or one or more tapering portions. Thus, one or more portions of the fixture may have e.g. thread tops lying in a common imaginary cylindrical surface, which cylindrical surface is parallel with the longitudinal axis of the fixture. Alternatively or additionally, one or more portions of the fixture may have thread tops lying in an imaginary conical surface which in the apical direction is tapering towards the longitudinal axis.

The externally threaded fixture may comprise one or more thread spirals.

The term "pitch" is used to indicate the axial distance between adjacent tops of a threading. The term "lead" is used to indicate the distance advanced parallel to the longitudinal axis when the fixture is turned one revolution, i.e. it corresponds to the pitch multiplied with the number of thread spirals. For a single thread spiral having a constant pitch, the lead is equal to the pitch; for a double thread spiral, the lead is twice the pitch.

The term "microthread" is used to indicate a thread having a height which is no greater than 0.2 mm. According to at least one example embodiment, the fixture is provided with microthreads having a height in the range of 0.02-0.2 mm, such as 0.05-0.015 mm, for instance 0.1 mm. The term "macrothread" is used to indicate a thread having a height which is greater than 0.2 mm. According to at least one example embodiment, the fixture is provided with macrothreads having a height in the range of 0.25-0.35 mm, such as 0.3 mm.

Suitably, microthreads may be located coronally of macrothreads. For instance, microthreads may be arranged to engage dense cortical bone and macrothreads may be arranged to engage porous spongious/cancellous bone. The lead of a microthread suitably corresponds to the lead of a macrothread. The macrothread pitch may, as an example, be 2-4 times, such as 3 times, the pitch of the microthreads. The pitch (top-to-top spacing) at a fixture portion provided with microthreads may be around 0.10-0.30 mm, for instance 0.20-0.24 mm. The pitch (top-to-top spacing) at a fixture portion provided with macrothreads may be around 0.30-0.90 mm, for instance 0.60-0.72 mm.

Microthreads can be regarded as defined, oriented roughness. A non-oriented roughness having smaller dimensions, for instance obtained by blasting, etching, etc., may be superimposed on microthreads as well as on macrothreads.

A thread profile may comprise two flanks, a top interconnecting said two flanks, a bottom formed between two adjacent threads, said flanks forming an acute angle v with a plane which is perpendicular to the fixture axis and which angle v lies in a plane containing the extension of the fixture axis, said profile further having a height D. The top may be curved and may have a top radius. Suitably, for $10° \leq v < 35°$, the top radius is greater than $0.4 \times D$ and, for $35° \leq v < 55°$, the top radius is greater than $0.2 \times D$.

BRIEF DESCRIPTION OF THE DRAWINGS

FIG. 1A is a top view of the dental fixture in FIG. 1.

FIG. 1B is a bottom view of the first dental component shown in FIG. 1.

FIG. 1C is bottom view of the second dental component shown in FIG. 1.

FIG. 3A illustrates schematically s circumferential distribution of first and second indexing elements on a dental component according to one example embodiment.

FIG. 3B illustrates schematically a circumferential distribution of first and second indexing elements on a dental component according to one example embodiment.

FIG. 3C illustrates schematically a circumferential distribution of first and second indexing elements on a dental component according to one example embodiment.

FIG. 3D illustrates schematically a circumferential distribution of first and second indexing elements on a dental component according to one example embodiment.

FIG. 3E illustrates schematically a circumferential distribution of first and second indexing elements on a dental component according to one example embodiment.

FIG. 8 illustrates a dental component according to at least one example embodiment, which is to be connected to a dental fixture in a specific rotational orientation, wherein the dental component and the dental fixture together represent a dental implant according to at least one example embodiment of the invention.

FIG. 8A is a schematic illustration of the interface between the indexing elements of the dental component and the indexing elements of the dental fixture when these items have been connected.

FIG. 8B is a bottom view of the dental component in FIG. 8.

FIG. 9 illustrates a section of a fixture engagement portion of a dental component according to at least one example embodiment of the invention.

FIG. 9A illustrates a section of a fixture engagement portion of a dental component according to at least one example embodiment of the invention.

FIG. 9B illustrates a section of a fixture engagement portion of a dental component according to at least one example embodiment of the invention.

FIG. 9C illustrates a section of a fixture engagement portion of a dental component according to at least one example embodiment of the invention.

FIG. 10A illustrates a section of a fixture engagement portion of a dental component according to at least one example embodiment of the invention.

FIG. 10B illustrates a section of a fixture engagement portion of a dental component according to at least one example embodiment of the invention.

DETAILED DESCRIPTION OF THE DRAWINGS

Figure 5:
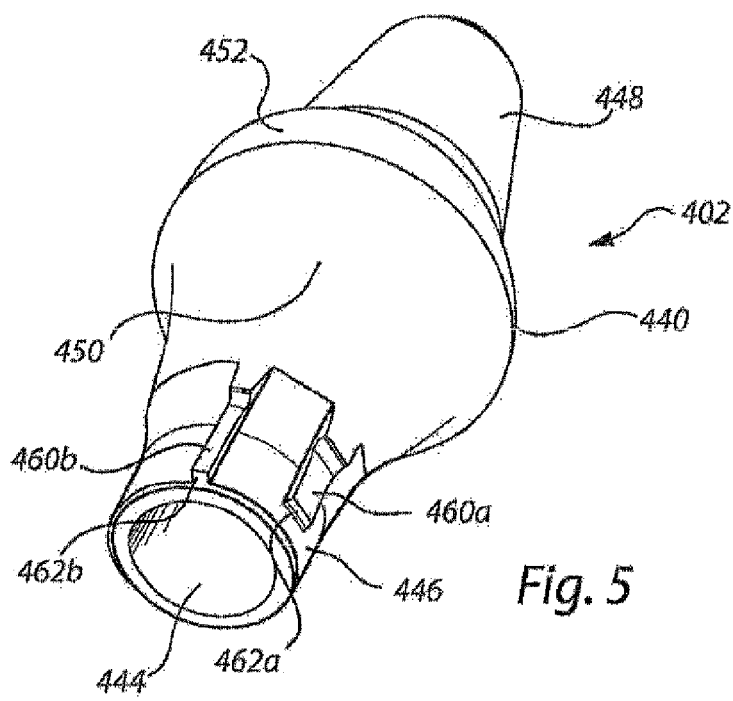
FIG. 5 illustrates a dental component according to at least one example embodiment of the invention.

Beginning with FIG. 5, a dental component 402 according to at least one example embodiment of the invention is illustrated. The dental component 402 may, for instance, be an abutment, an abutment replica or an abutment blank. The dental component 402 comprises a body part 440 which is provided with a central through-hole 444, through which a screw part (not shown) is insertable and connectible to internal threads of a dental fixture, in order to secure the body part to the fixture. The body part 440 comprises a fixture engagement portion 446, which is herein illustrated as having a generally cylindrical enveloping surface, although other enveloping surfaces, such as tapering, would be a conceivable alternatives. The body part 440 further comprises a dental crown-receiving or prosthesis-receiving portion 448 which extends coronally of the fixture above the gingiva. An extension portion 450, herein illustrated as coronally flaring up to a shoulder 452, is intended to extend through the gingiva and is provided between the fixture engagement portion 446 and the prosthesis-receiving portion 448. In case the dental component 402 is provided as an abutment blank, at least one of the extension portion 450 and the prosthesis-receiving portion 448 may be further processed to a desired shape, which may suitably be customized for the patient receiving the resulting processed abutment.

The fixture engagement portion 446 is provided with a radially projecting first indexing element 460a having an apical end 462a, and a radially projecting second indexing element 460b having an apical end 462b. The apical end 462b of the second indexing element 460b is located apically of the apical end 462a of the first indexing element 460a. The apical end 462b of the second indexing element 460b has a smaller dimension in the circumferential direction of the fixture engagement portion 446, compared to the apical end 462a of the first indexing element 460a. Indeed in this example embodiment, although not necessary, the entire second indexing element 460b is narrower than the first indexing element 460a.

Following the circumference of the fixture engagement portion 446, the first indexing element 460a is located at a position which is spaced from the position of the second indexing element 460b, i.e. the first indexing element 460a is circumferentially separated from the second indexing element 460b. Expressed differently, in a cylindrical coordinate system $(r, \phi, z)$ wherein the z axis coincides with the central geometrical axis of the engagement portion 446, the angle $\phi$ will be different for the first indexing element 460a and the second indexing element 460b.

The overall axial extension of the first indexing element 460a and the second indexing element 460b is such that the first indexing element 460a and the second indexing element 460b are intersected by a common geometrical plane which is perpendicular to the central axis of the fixture engagement portion 446. Thus, the axial extension of the first indexing element 460a is at least partly overlapped by the axial extension of the second indexing element 460b.

This dental component 402 may be connected to a dental fixture having indexing elements in the form of indexing indentations/recesses/depressions which sizewise match the first indexing element 460a of the dental component 402. Thus, as the dental component 402 is brought into contact with the fixture, the second indexing element 460b will be leading and will be the first to enter an associated indexing indentation in the fixture. Since the second indexing element 460b is underdimensioned there will be a certain play with respect to the indexing indentation and thus facilitate the mating. Once the second indexing element 460b has mated with its associated indexing indentation in the fixture, the trailing first indexing element 460a of the dental component 402 will be substantially aligned with its associated indexing indentation. Therefore, when the dental component 402 is continued to be inserted into the fixture, the first indexing element 460a will easily mate with its associated indexing indentation in the fixture. Since the fit between, the first indexing element 460a and its associated indexing indentation, provides less (if any) play, the rotational position of the dental component 402 will be well defined. Thus, the leading and underdimensioned second indexing element 460b has an initial guiding/aligning function while the trailing first indexing element 460a has the function of completing the rotational locking. For illustrative purposes, the first indexing element 460a and the second indexing element 460b have been arranged at a small distance from each other on the fixture engagement portion 446. However, in other embodiments, the spacing may be different, e.g. larger. Similarly, the skilled person understands that other shapes and dimensions of the indexing elements 460a, 460b are readily conceivable.

Figure 6:
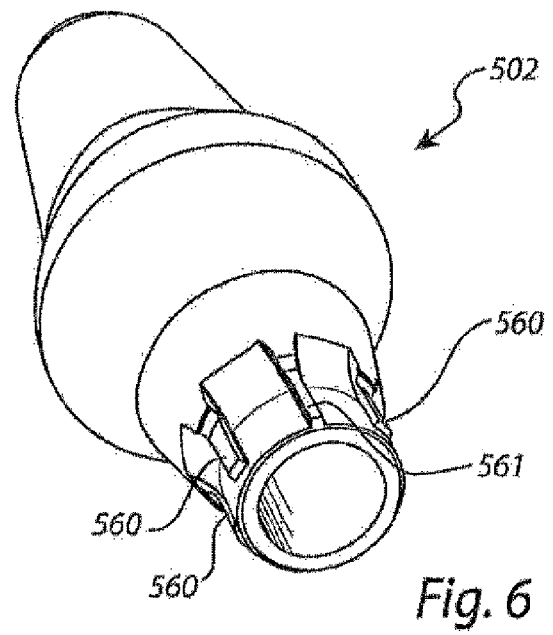
FIG. 6 illustrates a dental component according to at least one other example embodiment of the invention.

FIG. 6 illustrates a dental component 502 according to at least one other example embodiment of the invention. In this case, the dental component 502 is provided with five trailing first indexing elements 560 (only three are viewable in the figure) and one leading narrower second indexing element 561. The dental component 502 can, for instance, be connected to a dental fixture having six symmetrically distributed indexing elements in the form of indexing indentations/depressions/recesses. Thus, the dentist may select one of six rotational orientations for the dental component 502. When the dentist has determined the desired rotational orientation, the dental component 502 is connected to the dental fixture, by having the leading underdimensioned second indexing element 561 be the first one to mate with the associated indexing indentation in the fixture. The trailing five first indexing elements 560 will then mate their associated indexing indentations in the fixture.

While the dental component 502 in FIG. 6 illustrate a symmetrical distribution of indexing elements 560, 561 around the fixture engagement portion, allowing different rotational orientations relative to the dental fixture, there are other embodiments which are intended to only have one possible rotational orientation relative to a dental fixture. For instance, the dental component 402 in FIG. 5 can only be inserted in one rotational orientation if the mating dental fixture only has two corresponding indexing indentations. Other examples of embodiments with only one possible rotational orientation are presented in FIGS. 1-4 and FIG. 8.

Each drawing in FIGS. 1-4 and FIG. 8 illustrates a dental component having first and second indexing elements, and some of these drawings also illustrate a dental fixture having third and fourth indexing elements.

Figure 1:
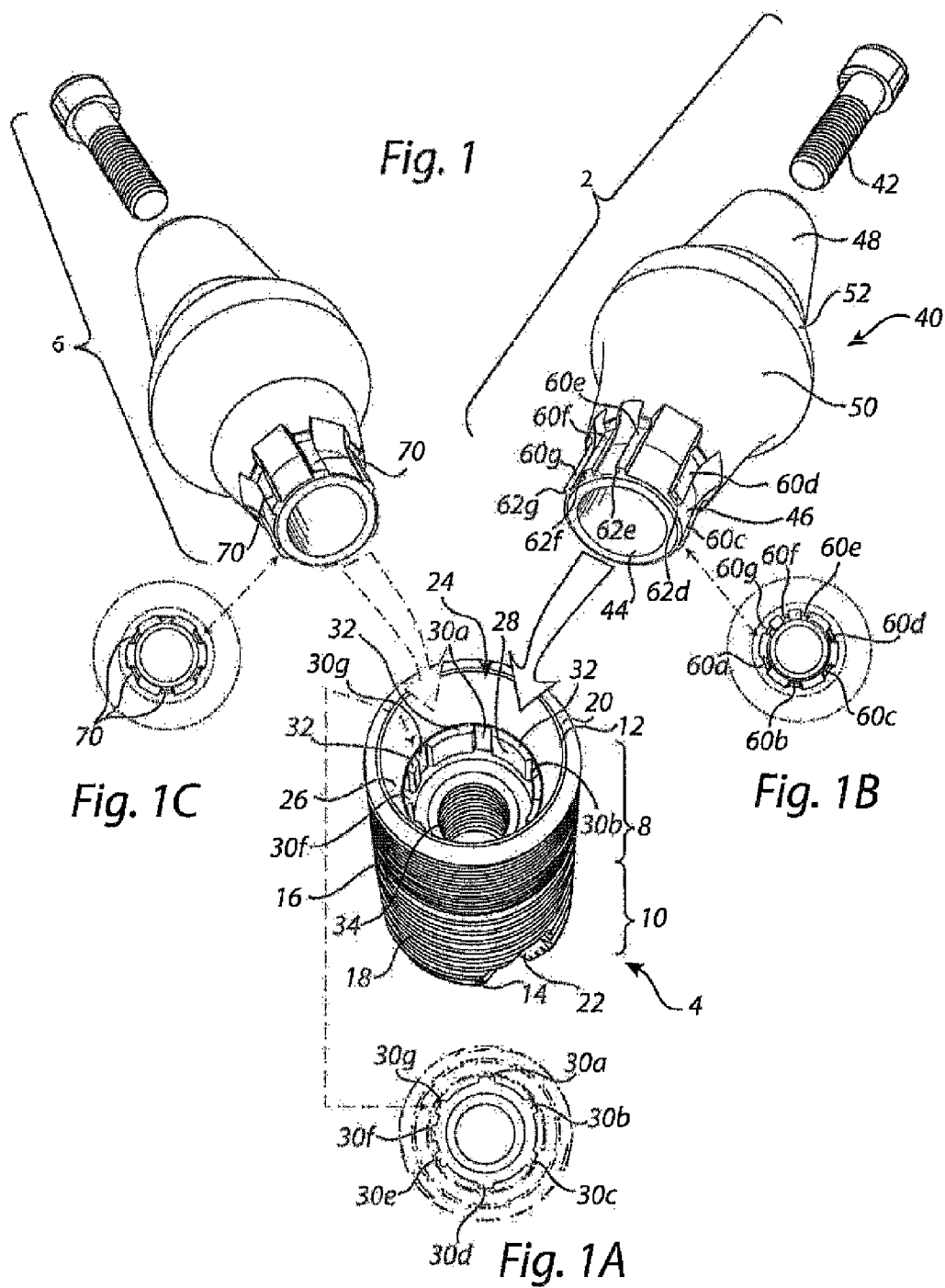
FIG. 1 is an exploded view of an implant system according to at least one example embodiment.

FIG. 1 illustrates a dental component 2 according to at least one example embodiment of the invention, which is to be connected to a dental fixture 4 in a specific rotational orientation with respect to the dental fixture 4, wherein the dental component 2 and the dental fixture 4 together represent a dental implant according to at least one example embodiment of the invention. FIG. 1 also illustrates another dental component 6 which may be arranged in a number of different rotational orientations with respect to the same dental fixture 4.

The herein illustrated dental fixture 4 has a coronal portion 8 extending apically from a coronal end 12 of the fixture 4, and an apical portion 10 extending coronally from an apical end 14 of the fixture 4.

The apical portion 10 may have a conicity tapering towards the apical end 14 of the fixture 4 to ease insertion of the fixture 4 into a bore-hole in the jawbone.

The fixture 4 has a core from which a surface structure projects, in the illustrated example being in the form of threads.

The coronal portion 8 is herein illustrated as being at least partly provided with microthreads 16, e.g. having three thread spirals, although another number is conceivable, such as 1, 2, 4 or more spirals. Although microthreads 16 have been illustrated, according to at least an alternative example embodiment the coronal portion 8 is at least partly provided with macrothreads 18, similarly to the apical portion 10, either as a separate thread spiral or as a continuation of the thread spiral at the apical portion 10. According to at least another alternative example embodiment, instead of microthreads 16, the coronal portion may be provided with a plurality of annular ridges, which to the naked eye could give the same visual appearance as microthreads. Other conceivable alternatives are circumferential lines of beads or non-oriented/randomly provided projections such as bulges.

In the illustrated example embodiment, the macrothreads 18 at the apical portion 10 has the same lead as the microthreads 16 at the coronal portion 8. However, the pitch of the macrothreads 18 is three times the pitch of the microthreads 16, since the microthreads 16 comprise three thread spirals.

The apical portion 10 comprising macrothreads 18 is herein illustrated as having one thread spiral, however, the apical portion 10 may alternatively have two or more thread spirals.

The length of the herein illustrated coronal portion 8 may be about 1-2 mm, such as 1.5 mm. However, shorter or longer lengths are readily conceivable. The relative length of the coronal portion 8 may also be selected from a wide range, such as 5-50% of the total length of the fixture 4, e.g. 10-20%.

The coronal portion 8 comprises a tapering end portion 20, which tapers towards the coronal end 12 of the fixture 4. The tapering end portion 20 is no more than 4% of the total length of the fixture 4. The surface of the tapering end portion 20 may be non-threaded, either smooth or blasted (or otherwise roughened).

Cutting recesses 22 or grooves extend coronally from the apical end 14. The number of cutting recesses 22 may be one or more, such as two, three or four cutting recesses, suitably symmetrically positioned about the circumference of the apical end 14 of the fixture 4 for self-tapping of the fixture 4 when being screwed/rotated into the bore-hole provided in the maxilla or mandible.

A socket 24 having an open end is provided in the coronal end 12 of the fixture 4. The socket 24 extends apically into the fixture 4. The socket 24 is for receiving a dental component 2 such as the illustrated abutment which will bridge the gingiva overlying the bore-hole and support/present a prosthetic part. However, it may also receive other dental components such as an abutment replica, a driver, a healing cap, an impression pick-up element, a digital transfer coping, etc.

Although various alternative configurations are conceivable, the socket 24 is herein illustrated as having a conical coronal section 26 and a substantially cylindrical intermediate wall section 28. Seven indexing elements 30a-30g, herein illustrated as radially extending recesses 30a-30g are provided in the intermediate wall section 28 (see also FIG. 1A). The intermediate wall section 28 and the radially extending recesses 30a-30g act as a component engagement portion of the fixture 4. The coronal end of the intermediate wall section 28 forms a shelf 32 with gaps formed by said seven recesses 30a-30g. Six of the recesses 30a-30e, 30g are equidistantly distributed along the circumference of the intermediate wall section 28. The seventh recess 30f is interposed between two (30e, 30g) of said six equidistantly distributed recesses. This is clearly illustrated in the top view of FIG. 1A.

The socket 24 is further provided with an internally threaded apical section 34.

A dental component 2 according to at least one example embodiment of the invention is herein illustrated as a two-piece abutment 2 consisting of a body part 40 and a screw part 42. The body part 40 of the abutment 2 is provided with a through-hole 44, wherein the screw part 42 is adapted to be inserted into the through-hole 44 and engage the internal thread 34 of the fixture 4 in order to secure the body part 40 to the fixture 4. The body part 40 comprises a fixture engagement portion 46, which is herein illustrated as having a generally cylindrical enveloping surface, although other enveloping surfaces, such as tapering, would be a conceivable alternatives. The body part 40 further comprises a dental crown-receiving or prosthesis-receiving portion 48 which extends coronally of the fixture 4 above the gingiva. An extension portion 50, herein illustrated as coronally flaring up to a shoulder 52, is intended to extend through the gingiva and is provided between the fixture engagement portion 46 and the prosthesis-receiving portion 48.

Seven indexing elements 60a-60g, herein illustrated as radial projections 60a-60g, are provided sequentially in the circumferential direction of the cylindrical enveloping surface of the fixture engagement portion 46 (see also FIG. 1B). Similarly to the distribution of the radial recesses 30a-30g in the fixture 4, there are six equidistantly distributed radial projections 60a-60e, 60g on the dental component 2, while the seventh radial projection 60f is interposed between two (60e, 60g) of said six equidistantly distributed radial projections. With this configuration, the seventh radial projection 60f and its two neighbouring radial projections 60e, 60g can only mate in one correct way with the seventh radial recess 30f and its two neighbouring recesses 30e, 30g. Thus, there is only one rotational orientation possible for the dental component 2 to be connected with respect to the dental fixture 4.

Four of the radial projections can be regarded as first indexing elements 60a-60d, each having an apical end (in FIG. 1 the apical end of the indexing element 60d is designated with reference numeral 62d). The other three radial projections 60e-60g, namely said seventh radial projection 60f and its two neighbouring projections 60e, 60g, can be regarded as second indexing elements 60e-60g having apical ends 62e-62g located apically of the apical ends of the first indexing elements 60a-60d. This facilitates for the dentist to connect the dental component 2 to the dental fixture 4 in the correct rotational orientation. In this example embodiment, contrary to the embodiment in FIG. 5, the number of first indexing elements 60a-60d is greater than the number of second indexing elements 60e-60g. In the circumferential direction of the fixture engagement portion 46, each one of the first indexing elements 60a-60d is located at a position which is different from the positions of the second indexing elements 60e-60g. Thus, each one of the first indexing elements 60a-60d is circumferentially separated from any one of the second indexing elements 60e-60g.

The close positioning of the second indexing elements 60e-60g results in that they are asymmetrically distributed along the circumference of the fixture engagement portion 46. Asymmetrical distribution means that the second indexing elements are not evenly distributed around the fixture engagement portion. An even, symmetrical distribution would have the three second indexing elements distributed at 120° from each other around the fixture engagement portion 46.

When the body part 40 of the abutment 2 is to be connected to the fixture 4, the projections forming said second indexing elements 60e-60g may come in contact with the shelf 32 in the fixture 4. The projections forming said first indexing elements 60a-60d will still be spaced from the shelf 32. The body part 40 is then rotated so that the second indexing elements 60e-60g fall into the designated recesses 30e-30g of the fixture 4, i.e. into the seventh recess 30f and its two neighbouring recesses 30e, 30g.

Thus, the second indexing elements 60e-60g will first engage with the seventh recess 30f and its two neighbouring recesses 30e, 30g which represent fourth indexing elements 30e-30g, and thereafter having already found the correct rotational position, the first indexing elements 60a-60d of the dental component 2 can engage with the third indexing elements 30a-30d (the other four recesses 30a-30d) of the dental fixture 4.

If only a single one (for example 60f) of the seven indexing elements 60a-60g of the dental component 2 would have an apical end located apically of the other six indexing elements, that single one (for example 60f) of the indexing elements 60a-60g could have mated with any one of the seven indexing elements 30a-30g of the fixture 4. However, only one (in this example 30f) of those seven indexing elements 30a-30g of the fixture is the correct one which allows the trailing indexing elements of the dental component to also mate with the corresponding indexing elements in the fixture. If the dentist would place said single one (e.g. 60f) of the seven radially projecting indexing elements 60a-60g into one of the six incorrect radially indented indexing elements (e.g. 30a-30e, 30g) trailing indexing elements (e.g. 60a-60e, 60g) of the dental component 2 would not find a mating indexing element in the fixture 4 but would abut the shelf 32. The dentist would have to lift the dental component 2 and try again to find the correct rotational orientation of the dental component 2 relative to the fixture 4. By additionally letting another one (for example 60g) of the seven indexing elements (60a-60g) have an apical end extending apically of the apical ends of the other indexing elements, said indexing element (in this example 60g) will be in contact with the shelf 32 of the fixture reducing the risk of the other indexing element (in this example 60f) falling into the incorrect recess in the fixture 4. Thus, having a dental component with at least one first indexing element and at least two second indexing elements having apical ends apically of the apical end of the first indexing element reduces the risk of the second indexing elements falling into the incorrect recesses in the fixture. Nevertheless, if the dentist brings the dental component 2 towards the fixture 4 in a slightly inclined direction, one of said second indexing elements may still be able to reach into an incorrect recess in the fixture, albeit not very deeply because of the other second indexing element contacting the shelf 32 preventing further advancement. Because the second indexing element cannot fall deeply into an incorrect recess, a rotating motion will easily lift the second indexing element and after continued rotation the correct position will be found.

Figure 2:
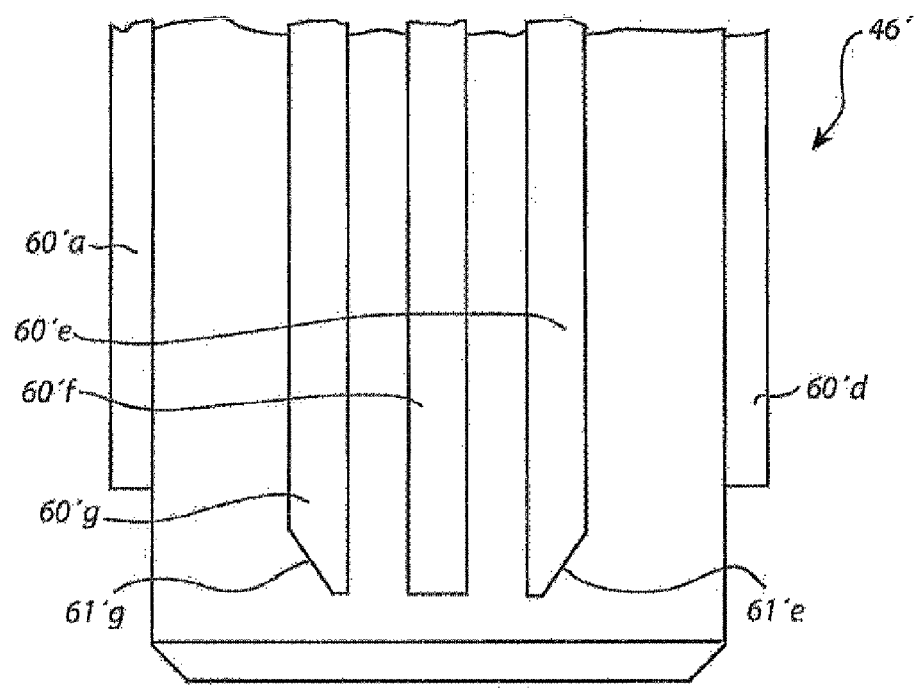
FIG. 2 illustrates a fixture engagement portion of a dental component according to at least one example embodiment.

Having three radially projecting second indexing elements with longer apical extensions than the trailing first indexing element further facilitates correct alignment of the indexing elements of the dental component with those of the fixture. FIG. 1 illustrates an advantageous distribution of three second indexing elements 60e-60g interposed between two (60a, 60d) of the first indexing elements 60a-60d. The middle one (60f) of the second indexing elements 60e-60g cannot fall into an incorrect recess (30a-30e, 30g) in the fixture 4, because of the other two (60e, 60g) second indexing elements provided on either side thereof. When the dental component 4 is to be connected to the fixture 2, the second indexing elements 60e-60g will with high likelihood land on the shelf 32, thus requiring the dentist to rotate the dental component 4 into the correct orientation. During such rotation, unless the dentist holds the dental component 4 absolutely straight, one of the two outer second indexing elements (60e, 60g) might just slightly drop into an incorrect recess in the fixture. Since the drop is so small, the dentist can easily continue the rotation until the correct alignment is found. Nevertheless, in FIG. 2, showing a fixture engagement portion 46' of a dental component, an example embodiment is illustrated in which each one of the two outer second indexing elements 60'e, 60'g are provided with a respective chamfer 61'e, 61'g on the side facing away from the middle one (60'f) of the second indexing element. Such a chamfer 61'e, 61'g further facilitates the continued rotating movement by the dentist in case one of the outer second indexing elements 60'e, 60'g would slightly drop into an incorrect recess. In FIG. 2, two shorter first indexing elements 60'a, 60'd are also visible. Also, it may be noted that the apical ends of the second indexing elements 60'e-60'g are not flush with the apical end of the dental component as in FIG. 1, but instead located somewhat coronally thereof.

As illustrated in the bottom view of FIG. 1B, the first indexing elements 60a-60d are somewhat wider than the second indexing elements 60e-60g. In the dental fixture 4, however, the third and fourth indexing elements 30a-30g have substantially the same width. This has the effect that due to a larger width difference between the second indexing elements 60e-60g and the fourth indexing elements 30e-30g, there will be a lateral play between these indexing elements facilitating the finding of the correct rotational orientation. In other words, because the radially projecting second indexing elements 60e-60g are laterally/transversely underdimensioned with respect to the radially indenting fourth indexing elements 30e-30g, they will more easily fall into place than if they were of substantially the same dimensions. The radially projecting first indexing elements 60a-60d are dimensionally closer matched to the radially indenting third indexing elements 30a-30d, reducing potential lateral play, and instead ensuring a substantially well-defined rotational position of the dental component 2 with respect to the dental fixture 4. It should be understood that rather than making the second indexing elements 60e-60g narrower than the first indexing elements 60a-60d, an option would be to make them of equal width and instead make the fourth indexing elements 30e-30g wider than the third indexing elements 30a-30d. Thus, the relatively large lateral play between the second and fourth indexing elements can be accomplished with various designs of the dental component and/or dental fixture.

In FIG. 1, the second indexing elements 60e-60g have been illustrated as extending all the way to the apical end of the body part 40, however, other alternatives are conceivable. For instance, the second indexing elements 60e-60g may extend somewhat shorter, as long as the apical ends 62e-62g thereof are located apically of the apical ends of the first indexing elements 60a-60d, or they may extend longer, i.e. beyond the apical end of the body part (see e.g. FIG. 2).

Furthermore, it should be noted that the coronal extension of the second indexing elements 60e-60g may also be shorter. In fact, it should be understood that, for the radially projecting second indexing elements 60e-60g to fall into connection with the radially indenting fourth indexing elements 30e-30g, the second indexing elements 60e-60g could be designed as substantially flat plates projecting from the surface of the fixture engagement portion 46 of the body part 40. Once the flat plates are received by the associated recesses 30e-30g, the whole body part 40, including the following indexing elements 60a-60d (i.e. the other radial projections which have the purpose to provide a rotational lock) will be guided in the desired direction for completing the insertion of the body part 40 into the dental fixture 4.

It should also be noted that, although second indexing elements 60e-60g have been presented in FIG. 1 as the seventh radial projection 60f and its two neighbouring radial projections 60e, 60g, other alternatives are possible. For instance, the seventh radial projection 60f and a non-neighbouring projection (such as projection 60a, 60b or 60c) could have their apical ends located apically of the apical ends of the other radial projections. These two radial projection would be leading and be the first ones to abut the shelf 32 provided between the recesses in the dental fixture 4. They can only fall down from the shelf when the seventh radial projection 60f is aligned with the seventh radial recess 30f. Thus, in general terms, according to at least one example embodiment, the distribution of the second indexing elements around the fixture engagement portion is asymmetrical relative to the distribution of the first indexing elements. In other words there is at least one pair of second indexing elements (for instance corresponding to the illustrated positions of 60f/60g, or 60f/60a, or 60f/60b) spaced differently than the spacing between any pair of first indexing elements.

FIG. 1 and FIG. 1C also illustrate another dental component 6 in the form of an abutment 6. It has six equally-dimensioned and equidistantly distributed indexing elements in the form of radial projections 70. Unlike the first abutment 2, this other abutment 6 lacks a seventh projection. Thus, this other abutment 6 may be connected to the dental fixture 4 in six different rotational orientations.

FIGS. 3A-3E illustrate schematically circumferential distributions of first and second indexing elements on dental components according to different example embodiments. Although not viewable from the drawings, in each of these example embodiments each one of the second indexing elements has an apical end located apically of the apical ends of the first indexing elements.

In FIG. 3A, the dental component is provided with one first indexing element 80 and two second indexing elements 81a, 81b. A radius $r_1$ from the central axis to the centre of said first indexing element 80 and a radius $r_2$ from the central axis to the centre of one 81a of the second indexing elements form a first angle $\theta$. A radius $r_3$ from the central axis to the centre of the other one 81b of said second indexing elements and said radius $r_1$ from the central axis to the first indexing element 80 form a second angle $\phi$. The second angle $\phi$ is different from said first angle $\theta$ and any angle being a multiple of said first angle $\theta$. In other words, $\phi \neq n\theta$, where n is a positive integer. The dashed line illustrate the contour of receiving indexing elements in the fixture. As can be seen not all of the indexing elements in the fixture are occupied by indexing elements of the dental component. Because of the asymmetry, the dental component can only mate in one correct rotational orientation with the fixture.

In connection with FIG. 3A, the following should be noted. The angle $\theta$ defining the positions of the first indexing element 80 and one 81a of the second indexing elements is illustrated as being 180°. Assuming a dental component would be manufactured differently, with the position of the first indexing element 80 and the position of the other one 81b of the second indexing elements being switched, then the two second indexing elements would have been located at 180° with respect to each other. If a dentist misplaces the dental component by 90°, the two oppositely located second indexing elements could enter receiving indexing elements in the fixture. However, the first indexing element would land on a shelf. When the dentist wishes to rotate the dental component to the correct position, he/she will experience a non-smooth, intermittent motion. However, the illustrated configuration in FIG. 3A, with the second indexing elements 81a, 81b being asymmetrically arranged will make the location finding process much smoother. Even if one of the second indexing elements would catch into an incorrect indexing element in the fixture, the other second indexing element will prevent it from falling too deeply, since both of the second indexing elements 81a, 81b have an apical end located apically of the apical end of the first indexing element 80.

In the embodiment of FIG. 3B, an additional second indexing element 81c is provided, compared to the embodiment in FIG. 3A. The three indexing elements 81a-81c makes the location finding even smoother.

In the embodiment of FIG. 3C, the dental component is provided with five first indexing elements 80a-80e and two second indexing elements 81a, 81b. The five first indexing elements 80a-80e and one 81a of the second indexing elements are equidistantly arranged at 60° intervals. The other one 81b of the second indexing elements is interposed and spaced at 30° from its neighbouring indexing elements 80e, 81a. The previously described first angle $\theta$ will, depending on which one of the first indexing elements 80a-80e is selected as a reference point, have a value of n*60° in relation to one 81a of second indexing elements, where n=1, 2, 3, 4, 5. In FIG. 3C the first indexing element 80b has been chosen (n=2), wherein the first angle $\theta=120°$ and the second angle $\phi=150°$.

In the embodiment of FIG. 3D, the dental component is provided with two first indexing elements 80a, 80b and two second indexing elements 81a, 81b. Unlike in the previous illustrations, the two second indexing elements 81a, 81b are not neighboring to each other in FIG. 3D. The first angle $\theta=90°$ and the second angle $\phi=225°$. Thus, the relationship $\phi \neq n\theta$ is valid also for this example embodiment.

In FIG. 3E the distribution corresponds to that in FIG. 1, thus four first indexing elements 80a-80d and three second indexing elements 81a-81c. It is also similar to the distribution in FIG. 3C, with the exception that one of the first indexing elements has now been replaced by a second indexing element. The second indexing elements 81a-81c have a smaller dimension in the radial direction than the first indexing elements 80a-80d. Thus, when placed in a fixture having substantially uniformly recessed indexing elements, there will be a larger play in the radial direction between the second indexing elements 81a-81c and the walls of the mating indexing element in the fixture than any play in the radial direction between the first indexing elements 80a-80d and the walls of their mating indexing elements. Once the correct rotational position is found, the larger play facilitates insertion of the second indexing elements 81a-81c into the mating recessed indexing elements of the fixture.

Figure 4:
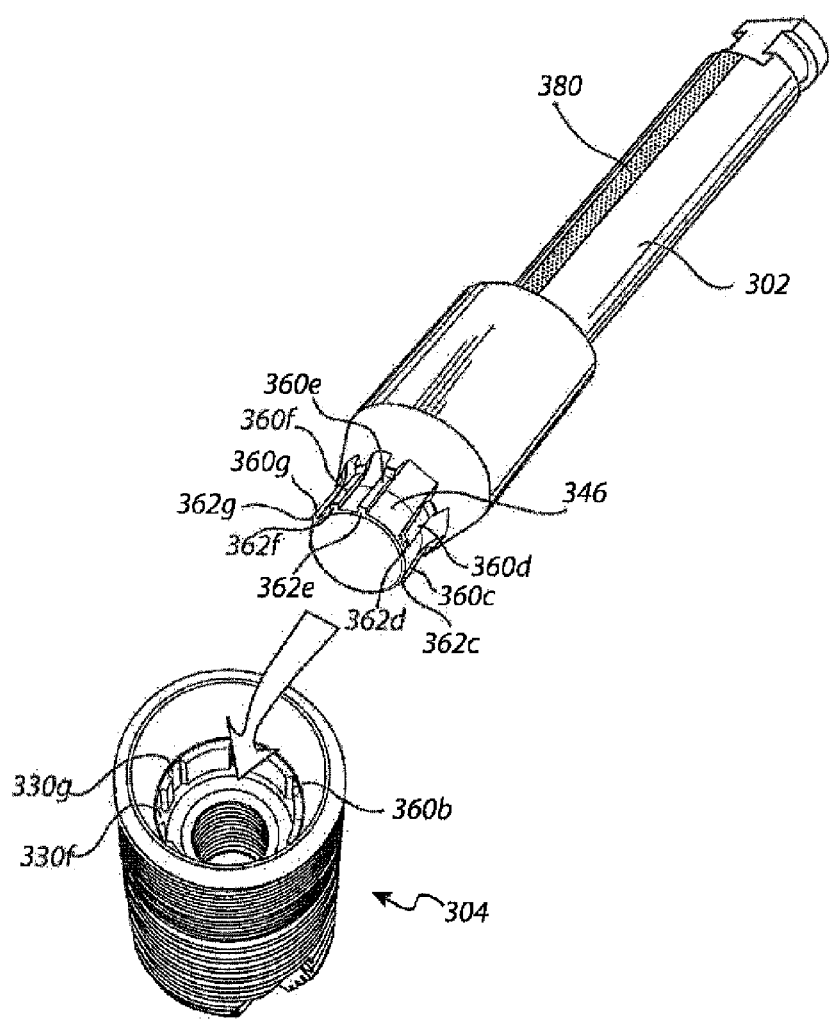
FIG. 4 illustrates, in accordance with at least one example embodiment, a dental component in the form of a driver to be connected to a dental fixture.

FIG. 4 illustrates, in accordance with at least one example embodiment, a dental component in the form of a driver 302 to be connected to a dental fixture 304. In this example, the interface between the dental fixture 304 and the driver 302 corresponds to the interface between the dental fixture 4 and dental component 2 illustrated in FIG. 1. Thus, the driver 304 has three radial projections (second indexing elements 360e-360g) having an apical end 362e-362g located apically of the apical ends (only 362c, 362d shown) of the other four radial projections (first indexing elements 360c, 360d; only two out of four can be seen in the perspective view shown in FIG. 4). The fixture has mating third and fourth indexing elements, respectively (only one third indexing element 330b and two fourth indexing elements 330f and 330g can be seen in this view). Thus, similarly to the connection in FIG. 1, the driver 302 can only be connected in one rotational orientation relative to the fixture 304.

The driver 302 is used for rotatingly driving the fixture 304 into a bore hole in the jawbone. The driver may be designed as a piece which can be used on its own, or alternatively, at its coronal end, the driver may be designed to be connectible to a handle, a wrench (such as a ratchet wrench), a power driver machine, etc.

The driver 302 is provided with a visually distinctive marking 380, herein illustrated as an axial line, aligned with the middle second indexing element 360f at the fixture engagement portion 346 of the driver 302. The distinctive marking 380 may have a color which is different from the rest of the driver 302, it may have different texture, or be slightly bulging, or any other appropriate viewable distinction compared to the rest of the driver.

The driver 302 can only be positioned in a single rotational indexing position relative to the fixture 304, meaning that each time the driver 302 engages such a fixture 304, the rotational position of the distinctive marking 380 relative to the fixture 304 will always be the same. Thus, by viewing the axial line provided by the marking 380, a user will be able to deduce the rotational position of the fixture 304 in the jawbone. This allows pre-planning and designing of the surgical and laboratory procedure before a dental fixture 304 is even inserted into the bone. For instance, a scan of the tooth-less site can be made, and a complete patient-specific implant may be designed in which the abutment should have a certain orientation relative to the fixture 304 and relative to the surrounding tissue, and therefore the fixture 304 should have a certain orientation in the jawbone.

A driver, such as the driver 302 illustrated in FIG. 4, may suitably be used with other dental fixtures. According to at least one example embodiment, the driver adapted to be connected to a dental fixture having a coronal end portion which is not flat. For instance, the fixture may have a sloped coronal end portion, in which the length of the fixture is greater on the lingual side than on the buccal side in order to match the contour of the jawbone. During installation of the fixture in the jawbone, the distinctive marking of the driver will indicate to the dentist in which direction the coronal end portion of the fixture is sloping, thus allowing the dentist to make appropriate adjustments to correctly align the slope of the fixture with the slope of the jawbone.

FIG. 8 illustrates a dental component 102 according to at least another example embodiment, which is to be connected to a dental fixture 104 in a specific rotational orientation, wherein the dental component 102 and the dental fixture 104 together represent a dental implant according to at least one other example embodiment of the invention. FIG. 8A is a schematic illustration of the interface between the indexing elements of the dental component and the indexing elements of the dental fixture when these items have been connected. FIG. 8B is a bottom view of the dental component in FIG. 8.

In FIG. 8, the socket 124 of the dental fixture 104 is provided with four small radial recesses 130a-130d and one large radial recess 130e (see also FIG. 8A in which the fixture contour is illustrated with the dashed line). Comparing with the dental fixture 4 in FIG. 1, the large recess 130e in FIG. 8 spans over the same distance as the three recesses 30e-30g representing the fourth indexing elements in FIG. 1. Thus, in the example illustrated in FIG. 8, the four small recesses 130a-130d are regarded as said plurality of third indexing elements 130a-130d, while the large recess 130e is regarded as a fourth indexing element 130e.

Similarly in FIG. 8, the dental component 102, represented as an abutment 102 having a body part 140 and a screw part 142, has a fixture engagement portion 146 provided with four small radial projections 160a-160d representing a plurality of first indexing elements 160a-160d and one large radial projection 160e (here shown as having greater width than the other projections) representing a second indexing element 160e (see also FIG. 8B). Due to the overdimensioning of the radially projecting second indexing element 160e, it cannot mate with the four small recesses forming the radially indented third indexing elements 130a-130d. Thus, there is only one correct rotational orientation for the body part 140, i.e. the position in which the large projection (second indexing element 160e) engages with the large recess (fourth indexing element 130e), and the small projections (first indexing elements 160a-160d) engage with the small recesses (third indexing elements 130a-130d).

The second indexing element 160e has an apical end 162e located apically of the apical ends of the first indexing elements 160a-160d (in FIG. 8, the apical end of the first indexing element 160d is depicted with reference numeral 162d). If all apical ends would have been at the same level, a dentist might accidently place the small projections (first indexing elements 160a-160d) in incorrect recesses. This could, in particular, be the case if the body part 140 of the dental component 102 is inserted somewhat obliquely relative to the fixture axis. Although, the body part 140 cannot be fully inserted after such misplacement, and the dentist will probably note that something is wrong, the misplacement may cause some jamming which, of course, is a source of irritation for the dentist. Therefore, by having the second indexing element 160e with an apical end 162e located apically of the apical ends of the first indexing elements 160a-160d, it is not possible to place the first and/or second indexing elements in a wrong mating recess. At most, the large projection representing the second indexing element 160e, will abut the shelf 132 in the socket 124 of the fixture 104, and will eventually fall into place in the large recess (fourth indexing element 130e) after rotation of the body part 140. Only when this alignment between the second indexing element 160e and the fourth indexing element 130e has been achieved, will the first indexing elements 160a-160d be able to engage with the third indexing elements 130a-130d.

As can be seen in FIG. 8A, the play between the second indexing element 160e and the fourth indexing element 130e is larger than any play between the first indexing elements 160a-160d and the respective third indexing elements 130a-130d. Thus, the fourth indexing element 130e in the fixture 104 has been overdimensioned in order to allow the second indexing element 160e of the dental component 102 to be easily received. The tighter fit between the first indexing elements 160a-160d and the third indexing elements 130a-130d achieves the desired rotational locking.

Figure 7:
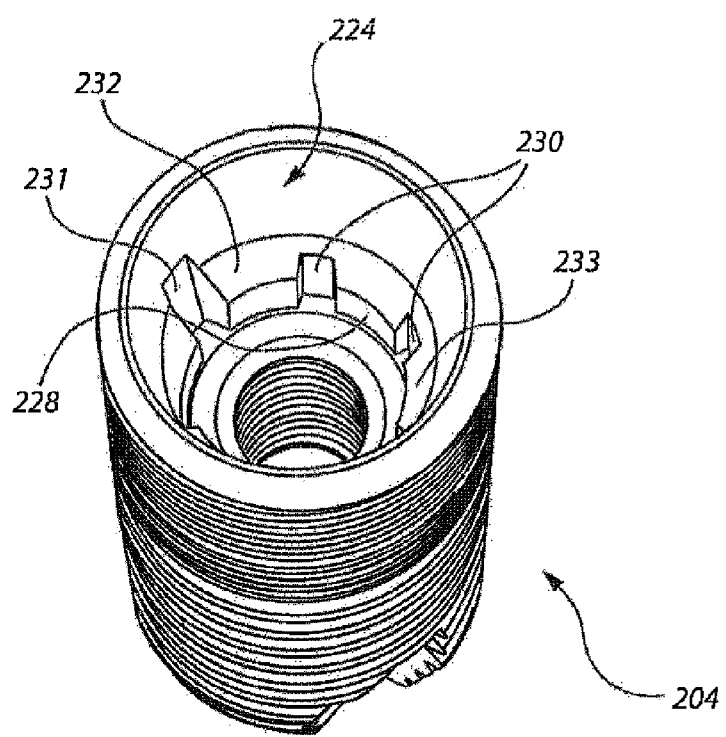
FIG. 7 illustrates a dental fixture according to at least one example embodiment of the invention.

FIG. 7 illustrates a dental fixture 204 according to at least one example embodiment of the invention.

In FIG. 7, the socket 224 of the dental fixture 204 is provided with six substantially evenly distributed radial indentations/depressions/recesses. Five of these radial recesses represent apical indexing elements 230. The sixth radial recess is wider than the other five recesses and represents a coronal indexing element 231. It should also be noted that the radial recesses 230, 231 are provided in an intermediate wall section 228 of the socket 224 to form a component engagement portion. The coronal end of that wall section 228 forms a shelf 232, 233. Said sixth narrow recess 231 has a coronal end located coronally of the coronal ends of the other five recesses 230. An area of the shelf is completely cut-away by said sixth recess 231, while the other five recesses 230 only provide a partial cut-out of the shelf. Furthermore, the areas 232 of the shelf next to the sixth recess 231 are located coronally of the other areas 233 of the shelf.

Thus, the sixth recess 231 (the coronal indexing element) will act to guide a mating indexing element of a dental component before the other recesses 230 (the apical indexing elements) will receive their respective mating indexing elements of the dental component for rotational locking.

FIGS. 9, 9A-9C and 10A-10B illustrate a section of a fixture engagement portion 510 of a dental component according to at least one example embodiment of the invention. The illustrated section of the fixture engagement portion 510 is tapering in the apical direction. The fixture engagement portion 510 is provided with a first radially projecting indexing element 520 and a second radially projecting indexing element 530. Viewed in isolation from the rest of the fixture engagement portion 510, the first indexing element 520 and the second indexing element 530 have identical dimensions in the circumferential and radial directions. Thus, their thickness and width are identical as can be seen in the cross-sectional views of FIGS. 9B and 10B (cross-sections taken along line B-B in FIGS. 9 and 10A, respectively). Additionally, as can be seen in FIGS. 9B and 10B the cross section of the indexing elements 520, 530 is substantially a trapezoid shape. This can also be seen in FIG. 9A, which is a cross-section taken along line A-A in FIG. 9.

The second indexing element 530 has an apical end 532 which is located apically of the apical end 522 of the first indexing element 520. Thus, when the dental component is brought into engagement with a component engagement portion 550 of a fixture having mating indexing indentations 560, 570 (illustrated with dashed lines), initially only the apical end 532 of the second indexing element 530 will enter the corresponding mating indexing indentation 570, as best seen in FIGS. 9 and 9C. After continued insertion (compare the views of FIGS. 9C and 10A) also the apical end 522 of the trailing first indexing element 520 will be inserted into its mating indexing element 560, as seen in FIG. 10A showing the first indexing element 520 partly inserted.

The radially most distant area of the apical end 522 of the first indexing element 520 is located at a distance R1 from the geometrical central axis x of the fixture engagement portion 550. Similarly, the radially most distant area of the apical end 532 of the second indexing element 530 is located at a distance R2 from the geometrical central axis x of the fixture engagement portion 550. Although, the first indexing element 520 and the second indexing element 530 have the same widths and thicknesses, because of the second indexing element 530 having its apical end 532 at the apical part of the tapered engagement portion 510, said radial distance R2 is shorter than said radial distance R1. This has the effect that a larger radial play is obtained for the second indexing element 530 than for the first indexing element 520 when entering their respective receiving indexing indentations 570, 560, which may be seen when comparing FIGS. 9B and 10B. Also, because of the trapezoid shape, even though that shape is the same for both indexing elements 520, 530, because they are located at different levels, one can note that there will also be a larger play in the circumferential direction for the second indexing element 530 when entering its indexing indentation 570.

Although the drawings have illustrated dental components provided with indexing elements in the form of radial projections and dental fixtures with indexing elements in the form of radial recesses, it should be understood that in other embodiments, the indexing elements of the dental components may instead be radial recesses and the indexing elements of the fixtures may be radial projections.

Furthermore, although the drawings have illustrated that the dental component as a male component having a fixture engagement portion to be inserted into a socket of the fixture (acting as a female component), other embodiments are also conceivable. For instance, the fixture may have a summit portion, which may suitably be adapted to extend beyond the bone crest, and apical end of the dental component may be provided with an socket extending coronally into the dental component, whereby the socket is intended to be placed onto the summit portion. Radially projecting or indenting indexing elements may be provided also for such a component/fixture interface.

Although the indexing elements have been illustrated as elongate radial projections and recesses, in other embodiments they would not be elongate. Furthermore, the cross-section of the indexing elements may be of any suitable shape, such as curved, triangular, rectangular, trapezoid, or any other regular or irregular shape.

It should also be noted that the number of indexing elements in the dental component does not necessarily have to be equal to the number of indexing elements in the dental fixture. For instance, in FIG. 1, one of the radial projections forming a first indexing element could be removed, although the effect of the rotational lock will be somewhat weakened.

The invention claimed is:
1. A dental implant, comprising
 a dental component comprising
  a fixture engagement portion provided with
   at least one first indexing element having an apical end, and
   a plurality of neighboring second indexing elements having an apical end, a dental fixture adapted to be inserted into a jawbone and comprising a component engagement portion adapted to mate with said fixture engagement portion, the component engagement portion being provided with
at least one third indexing element having a coronal end, and
a plurality of neighboring fourth indexing element having a coronal end,
wherein the apical end of each of the plurality of neighboring second indexing elements is located apically of the apical end of the first indexing element and
wherein the coronal end of each of the fourth indexing elements is located coronally of the coronal end of the third indexing element, and
wherein the first indexing element is only enabled to mate with the third indexing element after the plurality of neighboring second indexing elements have mated with the plurality of neighboring fourth indexing elements, and
wherein any play between the first indexing element and the mating third indexing element is smaller than a play between the plurality of neighboring second indexing elements and the plurality of neighboring fourth indexing elements, whereby a tighter fit is provided between the first and third indexing elements compared to the fit between the plurality of neighboring second and plurality of neighboring fourth indexing elements.

2. The dental implant as claimed in claim 1, wherein said plurality of neighboring second indexing elements are at least two second indexing elements asymmetrically distributed along the circumference of the fixture engagement portion.

3. The dental implant as claimed in claim 1, wherein said first and second indexing elements are provided as radial projections which project from a surface of the fixture engagement portion of the dental component, and wherein said third and fourth indexing elements are provided as radial depressions in a surface of the component engagement portion of the dental fixture.

4. The dental implant as claimed in claim 1, wherein the first, second, third and fourth indexing elements are distributed along the circumference of the fixture engagement portion and the component engagement portion, respectively, in such way that the dental component can only mate in one rotational orientation with respect to the dental fixture.

5. The dental implant as claimed in claim 1, wherein said at least one first indexing element is circumferentially separated from the plurality of neighboring second indexing elements, and wherein said at least one third indexing element is circumferentially separated from the plurality of neighboring fourth indexing elements.

6. A dental implant comprising:
a dental component including
a fixture engagement portion for engaging the dental component with a dental fixture adapted to be inserted into a jawbone or for engaging the dental component with a fixture replica, the fixture engagement portion having a geometrical central axis and being provided with
at least one radially projecting first indexing element having an apical end, and
a plurality of neighboring radially projecting second indexing elements, each one having an apical end located apically of the apical end of said first indexing element,
wherein the radially most distant area of the apical end of the plurality of neighboring second indexing elements is located at a shorter radial distance from said central axis than the radially most distant area of the apical end of the first indexing element, and
wherein the apical end of the plurality of neighboring second indexing elements has, compared to the apical end of the first indexing element, a smaller dimension in the circumferential direction of the fixture engagement portion, and
a dental fixture adapted to be inserted into a jawbone and comprising
a component engagement portion adapted to mate with said fixture engagement portion, the component engagement portion being provided with
at least one third indexing element having a coronal end, and
a plurality of neighboring fourth indexing elements, each one having a coronal end,
wherein the apical end of the plurality of neighboring second indexing elements is located apically of the apical end of the first indexing element and
wherein the coronal end of the plurality of neighboring fourth indexing elements is located coronally of the coronal end of the third indexing element,
wherein the first indexing element is only enabled to mate with the third indexing element after the plurality of neighboring second indexing elements have mated with the plurality of neighboring fourth indexing elements,
wherein any play between the first indexing element and the mating third indexing element is smaller than a play between the plurality of neighboring second indexing elements and the plurality of neighboring fourth indexing elements, whereby a tighter fit is provided between the first and third indexing elements compared to the fit between the plurality of neighboring second and plurality of neighboring fourth indexing elements.

* * * * *